(12) United States Patent
Fahrig et al.

(10) Patent No.: US 6,235,774 B1
(45) Date of Patent: May 22, 2001

(54) APPLICATION OF SUBSTITUTED AMINOMETHYL CHROMANS IN ORDER TO PREVENT NEURAL DEGENERATION AND TO PROMOTE NEURAL REGENERATION

(75) Inventors: Thomas Fahrig, Bergisch Gladbach; Irene Gerlach, Köln; Ervin Horváth, Leverkusen; Reinhard Jork, Haan, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/554,971

(22) PCT Filed: Nov. 11, 1998

(86) PCT No.: PCT/EP98/07197

§ 371 Date: May 23, 2000

§ 102(e) Date: May 23, 2000

(87) PCT Pub. No.: WO99/26621

PCT Pub. Date: Jun. 3, 1999

(30) Foreign Application Priority Data

Nov. 24, 1997 (DE) .............................. 197 51 949

(51) Int. Cl.⁷ .................................................. A61K 31/35
(52) U.S. Cl. ........................................... 514/456; 514/454
(58) Field of Search ...................... 514/454, 456

(56) References Cited

U.S. PATENT DOCUMENTS

| 5,468,753 | 11/1995 | Coude et al. | 514/277 |
| 5,468,882 | 11/1995 | Schohe-Loop et al. | 549/407 |
| 5,585,392 | 12/1996 | Junge et al. | 514/373 |
| 5,942,529 | 8/1999 | Schohe-Loop et al. | 514/373 |

FOREIGN PATENT DOCUMENTS

| 4135474 | 4/1993 | (DE) | C07D/311/58 |
| 0749970 | 12/1996 | (EP) | C07D/417/12 |

OTHER PUBLICATIONS

Carson, M. J., Thomas, E. A., Danielson, P. E., and Sutcliffe, J. G., "The 5–HT$_{5A}$ Serotonin Receptor is Expressed Predominantly by Astrocytes in Which it Inhibits cAMP Accumulation: A Mechanism for Neuronal Suppression of Reactive Astrocytes", GLIA, 17: 317–326 (1996).

Fahrig, T., "Changes in the Solubility of Glial Fibrillary Acidic Protein After Ischemic Brain Damage in the Mouse", Journal of Neurochemistry, 63(5): 1796–1801 (1994).

Reier, P. J., and Houle J. D., "The Glial Scar: Its Bearing on Axonal Elongation and Transplantation Approaches to CNS Repair", Advances in Neurology, 47: 87–138 (1988).

Riad, M., Emerit, M. B., and Hamon, M., "Neurotrophic Effects of Ipsapirone and Other 5–HT$_{1A}$ Receptor Agonists on Septal Cholinergic Neurons in Culture", Development Brain Research, 82: 245–258 (1994).

Welsh, F. A., Sakamoto, T., McKee, A. E., and Sims, R. E., "Effect of Lactacidosis on Pyridine Nucleotide Stability During Ischemia in Mouse Brain", Journal of Neurochemistry, 49(3): 846–851 (1987).

Whitaker–Azmitia, P. M., and Azmitia, E., "Stimulation of Astroglial Serotonin Receptors Produces Culture Media Which Regulates Growth of Serotonergic Neurons", Brain Research, 497: 80–85 (1989).

Whitaker–Azmitia, P.M., Murphy, R., and Azmitia, E.C., "Stimulation of Astroglial 5–HT$_{1A}$ Receptors Releases the Serotonergic Growth Factor, Protein S–100, and Alters Astroglial Morphology", Brain Research, 528: 155–158 (1990).

*Primary Examiner*—Amelia Owens
(74) *Attorney, Agent, or Firm*—Jerrie L. Chiu

(57) ABSTRACT

The invention relates to the use of substituted aminomethylchromans for the treatment of neuronal degeneration and for the promotion of neuronal regeneration in cerebral injuries and chronic disorders of the nervous system.

9 Claims, No Drawings

APPLICATION OF SUBSTITUTED AMINOMETHYL CHROMANS IN ORDER TO PREVENT NEURAL DEGENERATION AND TO PROMOTE NEURAL REGENERATION

The invention relates to the use of substituted aminomethyl-chromans for the production of medicaments for the prevention of degeneration of nerve cells (neurodegeneration) and for the promotion of neuronal regeneration (neuroregeneration) in the post-acute phase of cerebral injuries or in chronic disorders of the nervous system.

The nervous system of mammals consists essentially of two different cell classes: (a) the nerve cells (neurons) and (b) the glia cells, which for their part are divided again into oligodendrocytes, Schwann's cells, microglia and astrocytes.

After each disturbance of the integrity of the nervous system, astrocytes react in a stereotyped manner, which is described as reactive astrogliosis. This glial response can be triggered by a series of different injuries or disorders, such as, for example, surgical interventions, traumatic, immunological, chemical or ischaemic injuries or neurological disorders, such as Alzheimer's disease or Parkinson's disease. Reactive gliosis is characterized by the proliferation and hypertrophy of the cell bodies and cytoplasmic processes of astrocytes. The reaction of the astrocytes increases the expression of the astrocyte-specific constituent of the cell skeleton, glial fibrillary acidic protein (GFAP). During later phases, GFAP is the main constituent of the gliotic scar tissue, which results from the glial reaction. At present, the increased expression of GFAP is the only consistent characteristic of reactive gliosis.

The formation and persistence of glial scar tissue appears to be a main obstacle to the regeneration of nerve cells, since it inhibits the formation and the growth of neuronal processes both in vitro and in vivo (Reier and Houle, in *Advances in Neurology, Vol. 47: Functional Recovery in Neurological Diseases*, Raven Press, New York [1988], pages 87–138). The inhibition of the formation of the glial scar for the therapeutic treatment of various neurodegenerative and neurological disorders could therefore be a novel therapeutic principle.

Surprisingly, it appears that aminomethyl-chromans can reduce GFAP expression. The experiments were carried out in animals whose middle cerebral artery (MCA) was occluded and which are used as an animal model of stroke. These experiments indicated that aminomethyl-chromans can prevent the formation of glial scar tissue in vivo and thus can be therapeutically important for the treatment of neurodegenerative disorders which are characterized by the formation of glial scar tissue or by reactive gliosis, such as, for example, Parkinson's disease, amyotrophic lateral sclerosis or spinal cord disorders and/or injuries.

EP-A-0 352 613, EP-A-0 540 914 and EP-A-0 749 970 describe aminomethyl-chroman derivatives which are suitable for the prophylaxis, neuroprotection and treatment of formation of cerebral infarcts (cerebral apoplexy) such as stroke and cerebral ischaemia.

The therapeutic efficacy of the compounds described in these documents relates, however, to neuroprotection in the acute phase of the course of the disease. The acute sequelae of cerebral ischaemia, such as occurs, for example, after stroke, are reduced by use of neuroprotective drugs which contain the described aminomethyl-chromans as pharmacologically active constituents.

In contrast to this, however, it was an object of the present invention to make available compounds with regenerative potential which are suitable for the treatment of the post-acute phase of cerebral injuries or for the treatment of various chronic disorders of the nervous system.

The object is achieved according to the invention by the use of substituted aminomethyl-chromans of the following formula (I)

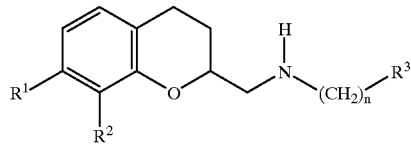

in which
$R^1$ represents hydrogen,
$R^2$ represents hydrogen, hydroxyl or a radical of the formula $-OCH_3$, $-OCH_2CH_3$, $-OCH(CH_3)_2$ or $-OCH_2C(CH_3)_2-Cl$, or
$R^1$ and $R^2$ together form a radical of the formula

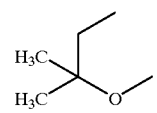

$R^3$ represents cyclopentyl, cyclohexyl, cycloheptyl, or the following radical, designated as o-benzenesulphimidyl:

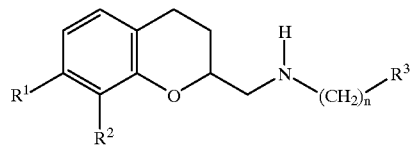

and
n is selected from 1, 2, 3, 4 or 5,
and their optical isomers and pharmaceutically acceptable salts,
for the production of a medicament for the treatment of neurodegenerative disorders and for the promotion of neuronal regeneration.

The principle of the preparation of the aminomethyl-chromans to be used according to the invention is disclosed in EP-A-0 352 613, EP-A-0 540 914 or EP-A-0 749 970. In the context of the present invention, the compounds can be present in various stereoisomeric forms, i.e. in the form of their (+) or (−) enantiomers or as a mixture of these enantiomers (racemate). For the separation of the racemates into the enantiomeric forms, reference is made to the relevant, known specialist literature. A preferred compound is the (−) enantiomer of the compound of the formula (I) in which $R^1$ and $R^2$=hydrogen, $R^3$=o-benzenesulphimidyl and n=4.

In the context of the present invention, the physiologically acceptable salts can also be employed. Physiologically acceptable salts of the substituted 2-aminomethyl-chromans can be salts of the compounds according to the invention with suitable organic or inorganic acids, in particular mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Compounds of the general formula (I) and the pharmaceutical compositions derived from these compounds can be used for the post-acute therapeutic treatment of a variety of neurological conditions in which various cell types of the nervous system are degenerated and/or have been damaged as a result of neurodegenerative disorders or injuries or exposures. In particular, compounds of the general formula (I) can be used for the treatment of resulting conditions, in which damage to cells of the nervous system has occurred due to surgical interventions, infections, exposure to toxic agents, tumours, nutritional deficits or metabolic disorders. In addition, compounds of the general formula (I) can be used for the treatment of the sequelae of neurodegenerative disorders, such as Parkinson's disease, multiple sclerosis, amyotrophic lateral sclerosis, epilepsy, drug abuse or drug addiction (alcohol, cocaine, heroin, amphetamine or the like), spinal cord disorders and/or injuries, dystrophy or degeneration of the neural retina (retinopathies) and peripheral neuropathies, such as diabetic neuropathy and/or the peripheral neuropathies induced by toxins. In addition, compounds of the general formula (I) can be used in combination with surgical implantations of tissues and/or prostheses for the treatment of Alzheimer's disease or other neurological disorders and/or malfunctions in which implantation is indicated.

Preferred compounds in the context of the invention are those of the general formula (I),
where
$R^1$ represents hydrogen,
$R^2$ represents hydrogen, hydroxyl or a radical of the formula
—OCH$_3$, —OH(CH$_3$)$_2$ or —OCH$_2$C(CH$_3$)$_2$—Cl or,
$R^1$ and $R^2$ together form a radical of the formula

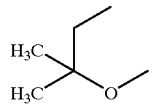

$R^3$ represents o-benzenesulphimidyl,
n=3 or 4;
and aminomethyl-chromans of the general formula (I)
in which
$R^1$ represents hydrogen,
$R^2$ represents hydrogen, hydroxyl or a radical of the formula
—OCH$_3$ or —OCH(CH$_3$)$_2$, or
$R^1$ and $R^2$ together form a radical of the formula

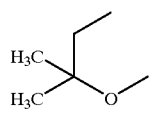

n=1 and
$R^3$ represents cyclohexyl or cycloheptyl.
Particularly preferred compounds are those of the general formula (I),
where
$R^1$ represents hydrogen, and
$R^2$ represents hydrogen or a radical of the formula —OCH$_3$, —OCH(CH$_3$)$_2$ or —OCH$_2$C(CH$_3$)$_2$—Cl, or $R^1$ and $R^2$ together form a radical of the formula

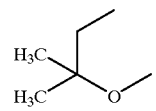

$R^3$ represents o-benzenesulphimidyl, and
n=4;
and aminomethyl-chromans of the general formula (I)
in which
$R^1$ represents hydrogen,
$R^2$ represents hydrogen or —OCH$_3$,
n=1,
and
$R^3$ represents cyclopentyl.

It is generally preferred that if $R^3$=o-benzenesulphimidyl, n=3, 4 or 5, particularly preferably 3 or 4.

The active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this connection, the therapeutically active compound should in each case be present in a concentration from approximately 0.1 to 95% by weight, preferably from approximately 0.5 to 90% by weight, of the total mixture, i.e. in amounts which are sufficient in order to achieve the dose range indicated.

The formulations are prepared, for example, by extending the active compounds using solvents and/or excipients, if appropriate using emulsifying agents and/or dispersing agents, where, for example, if the diluent used is water, organic solvents can optionally be used as auxiliary solvents.

The auxiliaries can be selected, for example, from the group comprising water, non-toxic organic solvents, such as paraffin (e.g. petroleum fractions), vegetable oils (e.g. peanut/sesame oil), alcohols (e.g. ethyl alcohol, glycerol), excipients, such as, for example ground natural minerals (e.g. kaolins, argillaceous earths, talc, chalk), ground synthetic minerals (e.g. highly dispersed silicic acid, silicate), sugars (e.g. cane sugar, lactose and dextrose), emulsifying agents (e.g. polyoxyethylene fatty acid esters, polyoxyethylene fatty alcohol ethers), dispersing agents (e.g. lignin sulphite waste liquors, methylcellulose, starch and polyvinylpyrrolidone) and lubricants (e.g. magnesium stearate, talc, stearic acid and sodium sulphate).

Administration is carried out in a customary manner, preferably orally or subcutaneously, in particular intramuscularly or intravenously. In the case of oral administration, apart from the excipients mentioned tablets can, of course, also contain additions, such as sodium citrate, calcium carbonate or dicalcium phosphate together with various additives, such as starch, preferably potato starch, gelatine and the like. Furthermore, lubricants, such as magnesium stearate, sodium lauryl sulphate and talc can additionally be used for tableting. In the case of aqueous suspensions, apart from the above-mentioned auxiliaries, the active compounds can be treated with various flavour enhancers or colorants.

In general, it has proven advantageous in the case of intravenous administration to administer amounts from approximately 0.001 to 1 mg/kg, preferably approximately 0.01 to 0.5 mg/kg, of body weight every 24 hours to achieve efficacious results. In the case of oral administration, the dose is approximately 0.01 to 20 mg/kg, preferably 0.1 to 10 mg/kg, of body weight every 24 hours. Administration can in each case be carried out in the form of individual doses.

Despite this, where appropriate it may be necessary to deviate from the amounts mentioned, namely depending on the body weight or the type of administration route, on individual behaviour towards the medicament, the manner of its formulation and the time or interval at which administration takes place. Thus in some cases it may be adequate to manage with less than the above-mentioned minimum amount, while in other cases the upper limits mentioned have to be exceeded. In the case of the administration of relatively large amounts, it may be advisable to divide these into several individual doses over the course of the day.

The invention is illustrated in greater detail by the following example.

EXAMPLE

In the present example, the test substance was administered during the acute phase of the injury process in order to achieve its optimum action. However, the substance effect on the chronic phase of the course of the illness was assessed, so that the results definitely point to the potential of the test substance for the treatment of chronic damage. Occlusion of the middle cerebral artery (MCA-O)

Unilateral cerebral ischaemia was induced in tribromoethanol-anaesthetized mice by permanent occlusion of the middle cerebral artery (MCA). The operation was carried out according to known methods (Welsh et al., *J Neurochem.* 49, pages 846–851 [1987]) and leads to infarction of cortical and subcortical regions of the ipsilateral cerebral hemisphere which is supplied by the left MCA.
Determination of the GFAP immunoreactivity Seven days after operation, the animals were sacrificed by decapitation, the brains were removed, protein fractions were prepared and the GFAP immunoreactivity in the "soluble" protein fraction was determined as described (Fahrig, *J Neurochem.* 63, pages 1796–1801 [1994]). The determined GFAP content of the contralateral cerebral hemisphere was set equal to 100% (control) and the GFAP content of the ipsilateral cerebral hemisphere (i.e. the hemisphere which includes the infarct region) was calculated in relation thereto.
Treatment with test substance In this example, the (−) enantiomer of the compound of the general formula (I) was used, where $R^1$ and $R^2$=hydrogen, $R^3$=o-benzenesulphimidyl and n=4. The compound was dissolved in a citrate-buffered (citric acid/sodium citrate) physiological saline solution and administered by multiple i.v. injections immediately, 2 and 4 hours after the operation. Under these conditions, the compound reduced the ischaemia-induced GFAP immunoreactivity (and thus the glial scar formation) in a dose-dependent manner (Table 1).

TABLE 1

Reduction of the GFAP immunoreactivity by an aminomethyl-chroman of the general formula (I) where $R^1$ and $R^2$ = H, $R^3$ = o-benzenesulphimidyl, n = 4

| Dose | 1 μg/kg | 10 μg/kg | 30 μg/kg | 100 μg/kg |
|---|---|---|---|---|
| GFAP immunoreactivity [% of the control] | 94.0 | 79.7 | 62.3 | 59.5 |
| S.E.M. *[%] | 3.2 | 9.2 | 8.5 | 3.4 |
| Reduction of the GFAP immunoreactivity [%] | −6.0 | −20.3 | −37.7 | −40.5 |

*Standard error of the mean

What is claimed is:

1. A method of treating a neurological condition resulting from surgical interventions, infections, implantations, exposure to toxic agents, tumors, nutritional deficits or metabolic disorders, multiple sclerosis, amyotrophic lateral sclerosis, epilepsy, drug abuse or drug addiction, spinal cord disorders or injuries, dystrophy or degeneration of the neural retina, or peripheral neuropathies, comprising administering to a patient in need thereof an effective amount of a substituted aminomethyl-chroman of the following formula (I)

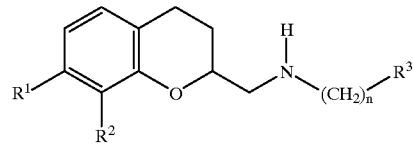

wherein,
$R^1$ represents hydrogen,
$R^2$ represents hydrogen, hydroxyl or a radical of the formula —$OCH_3$, —$OCH_2CH_3$, —$OCH(CH_3)_2$ or —$OCH_2C(CH_3)_2$—Cl, or
$R^1$ and $R^2$ together form a radical of the formula

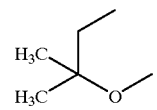

$R^3$ represents cyclopentyl, cyclohexyl, cycloheptyl, cyclooctyl or o-benzenesulphimidyl and
n is selected from 1, 2, 3, 4 or 5,
and their optical isomers and pharmaceutically acceptable salts.

2. A method of treating a neurological condition resulting from Alzheimer's disease, comprising administering to a patient in need thereof an effective amount of a substituted aminomethyl-chroman of the following formula (I) in combination with surgical implantations and/or prostheses:

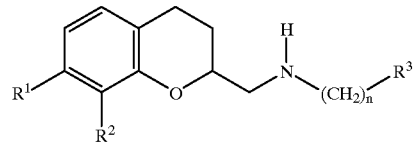

wherein
$R^1$ represents hydrogen
$R^2$ represents hydrogen, hydroxyl or a radical of the formula —$OCH_3$, —$OCH_2CH_3$, —$OCH(CH_3)_2$ or —$OCH_2C(CH_3)_2$—Cl, or
$R^1$ and $R^2$ together form a radical of the formula

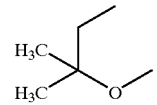

$R^3$ represents cyclopentyl, cyclohexyl, cycloheptyl, cyclooctyl or o-benzenesulphimidyl and
n is selected from 1, 2, 3, 4 or 5,
and their optical isomers and pharmaceutically acceptable salts.

3. A method of regeneratively treating a neurological condition resulting from Parkinson's disease, comprising administering to a patient in need thereof an effective amount of a substituted aminomethyl-chroman of the following formula

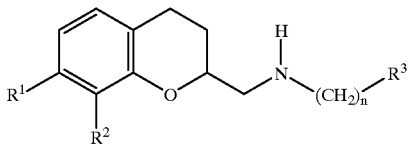
(I)

wherein
R¹ represents hydrogen,
R² represents hydrogen, hydroxyl or a radical of the formula —OCH₃, —OCH₂CH₃, —OCH(CH₃)₂ or —OCH₂C(CH₃)₂—Cl, or
R¹ and R² together form a radical of the formula

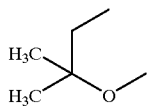

R³ represents cyclopentyl, cyclohexyl, cycloheptyl, cyclooctyl or o-benzenesulphimidyl, and
n is selected from 1, 2, 3, 4 or 5,
and their optical isomers and pharmaceutically acceptable salts.

4. The method of claim 1, 2 or 3, wherein n=3, 4 or 5 and R³ is o-benzenesulphimidyl.

5. The method of claim 1, 2 or 3, wherein
R¹ represents hydrogen,
R² represents hydrogen or a radical of the formula —OCH₃, —OCH(CH₃)₂ or —OCH₂C(CH₃)₂—Cl or R¹ and R² together form a radical of the formula

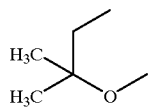

R³=o-benzenesulphimidyl and n=4.

6. The method of claim 1, 2 or 3, wherein
R¹ represents hydrogen,
R² represents hydrogen, —OCH₃ or —OCH(CH₃)₂, or
R¹ and R² taken together form a radical of the formula

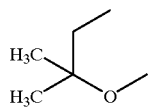

R³ represents cyclohexyl or cycloheptyl, and
n=1.

7. The method of claim 6, wherein
R¹ represents hydrogen,
R² represents hydrogen or —OCH₃,
R³ represents cycloheptyl, and
n=1.

8. The method of claim 1, 2 or 3, wherein
R¹ and R² represent hydrogen,
R³ represents o-benzenesulphimidyl, and
n=4.

9. The method of claim 1, 2 or 3, wherein the substituted aminomethyl-chroman of formula (I) has the (−) enantiomer configuration.

* * * * *